United States Patent
Guala (10) Patent No.: US 10,279,160 B2
(45) Date of Patent: May 7, 2019

(54) SAFETY CAP FOR MEDICAL DEVICES (71) Applicant: Industrie Borla S.p.A., Moncalieri (Turin) (IT)

(72) Inventor: Gianni Guala, Turin (IT)

(73) Assignee: INDUSTRIE BORLA S.P.A., Moncalieri (Turin) (IT)

( * ) Notice: Subject to any disclaimer, the term of this patent is extended or adjusted under 35 U.S.C. 154(b) by 179 days.

(21) Appl. No.: 15/325,953

(22) PCT Filed: Jul. 21, 2014

(86) PCT No.: PCT/IB2014/063285
§ 371 (c)(1),
(2) Date: Jan. 12, 2017

(87) PCT Pub. No.: WO2016/012834
PCT Pub. Date: Jan. 28, 2016

(65) Prior Publication Data
US 2017/0151426 A1 Jun. 1, 2017

(51) Int. Cl.
*A61M 39/20* (2006.01)
*A61M 39/10* (2006.01)

(52) U.S. Cl.
CPC ........ *A61M 39/20* (2013.01); *A61M 39/1011* (2013.01); *A61M 2039/1033* (2013.01); *A61M 2039/1066* (2013.01); *A61M 2205/0216* (2013.01)

(58) Field of Classification Search
CPC .. A61M 2039/1016; A61M 2039/1033; A61M 39/1011; A61M 39/10; A61M 2205/6045; A61M 39/20
See application file for complete search history.

(56) References Cited

U.S. PATENT DOCUMENTS

2013/0187381 A1 7/2013 Guala
2013/0197485 A1 8/2013 Gardner et al.

FOREIGN PATENT DOCUMENTS

| DE | 4318101 A1 | 12/1994 |
| EP | 0443868 A1 | 8/1991 |
| EP | 1747797 A1 | 1/2007 |
| EP | 2620178 A1 | 7/2013 |

(Continued)

OTHER PUBLICATIONS

Patent Cooperation Treaty, Notification of Transmittal of the International Search Report and the Written Opinion of the International Searching Authority, or the Declaration for PCT/IB2014/063285, dated Mar. 20, 2015, 10 pages.

(Continued)

*Primary Examiner* — Bradley J Osinski
(74) *Attorney, Agent, or Firm* — Heslin Rothenberg Farley & Mesiti P.C.; Victor A. Cardona, Esq.

(57) ABSTRACT

A cap for medical fluid lines and the like includes a hollow body within which a male or female connector accessible at one end of the body is coaxially housed. The connector is configured to inviolably obstruct the passage through the body. A unidirectional coupling locks in rotation the connector with respect to the body in the direction corresponding to the screwing of the connector, and a complementary connector, and to enable free rotation of the connector in the opposite direction. The connector can be possibly locked in rotation with respect to the body in the unscrewing direction, only following a positive command.

7 Claims, 12 Drawing Sheets

(56) References Cited

FOREIGN PATENT DOCUMENTS

| | | |
|---|---|---|
| GB | 2379253 A | 3/2003 |
| JP | S53-161954 U | 5/1952 |
| JP | S54-22125 Y | 8/1979 |
| JP | 2006-230739 A | 9/2006 |
| JP | 2013-150805 A | 8/2013 |
| WO | 2014/191956 A1 | 12/2014 |

OTHER PUBLICATIONS

First Office Action (Translation) dated Apr. 17, 2018 in connection with corresponding Japanese Application No. 2017-501208.
Summary of First Office Action (Translation) dated Apr. 17, 2018 in connection with corresponding Japanese Application No. 2017-501208.

FIG. 23

SAFETY CAP FOR MEDICAL DEVICES

FIELD OF THE INVENTION

The present invention relates, in general, to medical lines, and to containers for medicinal substances, for example, chemotherapy and the like.

STATE OF THE ART

In such applications, it is necessary to be able to securely close the line or container so as to prevent accidental openings and leakage of substances that, if toxic, could lead to serious risks of contamination.

The currently known closing systems are not free from risks of accidental disengagement, which can also be due to incorrect operation by the operators.

SUMMARY OF THE INVENTION

The object of the present invention is to provide a safe and effective solution to this problem, whilst at the same time being practical and functional.

According to the invention, this object is achieved thanks to a safety cap for medical fluid lines and the like, whose unique characteristic lies in the fact that it comprises a hollow body within which a connector is coaxially housed, accessible at one end of the body and configured so as to obstruct the passage through the body in an inviolable manner. Unidirectional coupling means are provided to lock the connector in rotation with respect to the body, in the direction corresponding to the screwing of the connector and a complementary connector to be coupled therewith, and to allow the free rotation of said connector in the opposite direction.

Thanks to this solution idea, the invention provides a closing cap having a very high degree of safety against risks of undesired or accidental openings, or due to incorrect operation.

The cap according to the invention may further comprise locking means designed to be positively operated to lock the connector in rotation with respect to the body in the opposite direction of rotation, i.e. in the direction of unscrewing.

In a first embodiment of the invention, the connector of the cap is a male connector of the luer lock type or the like, having an internally threaded outer hollow element of a known manner, and an inner hollow element. The latter has a transverse partition for closing the flow through the fitting.

In a second embodiment of the invention, the connector of the cap is a female connector of the luer lock or the like, having an externally threaded hollow element, which has a transverse partition for closing the flow through the fitting.

BRIEF DESCRIPTION OF THE DRAWINGS

The invention will now be described in detail with reference to the accompanying drawings, provided purely by way of non-limiting example, in which.

DETAILED DESCRIPTION OF THE INVENTION

Referring initially to FIGS. 1 to 6, the safety cap according to a first embodiment of the invention is indicated with I and comprises an outer hollow body 1 of a generally cylindrical shape, within which a male connector 2 of the luer lock type and analogues is coaxially housed.

The male connector 2 is rotatably mounted relative to the body 1, with the limitations which will be discussed, and has a partly conventional structure. In detail, the male connector 2 comprises an inner tubular element 4 with a conical outer surface protruding from one end of the body 1, and an internally threaded outer hollow element 5, which extends towards the inside of the body 1 with a integral hollow sleeve-shaped appendage 6, locked axially within the body 1, which is conveniently formed from two half-shells joined together in an interlocking manner.

During use, the male connector 2 is intended to be coupled to a complementary female connector of the luer lock type or the like and, according to a first aspect of the invention, the inner tubular element 4 is closed at its free end by a transverse wall 7. Consequently, the flow passage through the cap I is permanently obstructed in an inviolable manner.

According to another aspect of the invention, the composite formed by the male connector 2 and the sleeve 6 is coupled in rotation in one direction with the body 1, and is freely rotatable in the opposite direction. However, as will become evident, the rotation in the opposite direction may also possibly be locked, but only following a positive command imparted manually.

Figure 1:
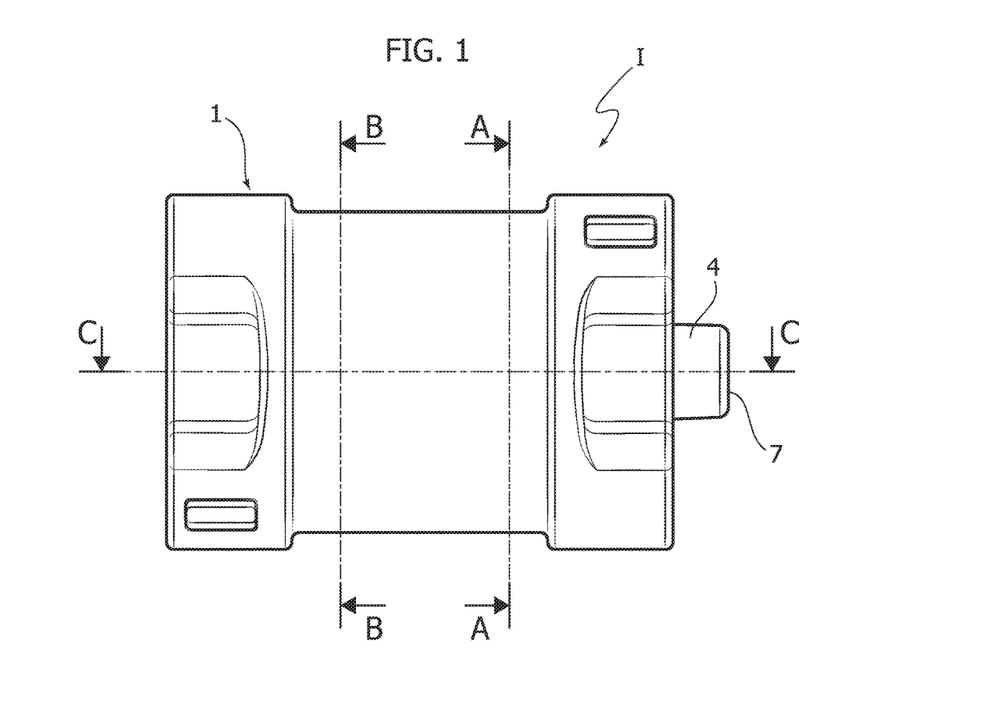
FIG. 1 is a schematic elevational side view of a safety cap according to a first embodiment of the invention.
Figure 2:
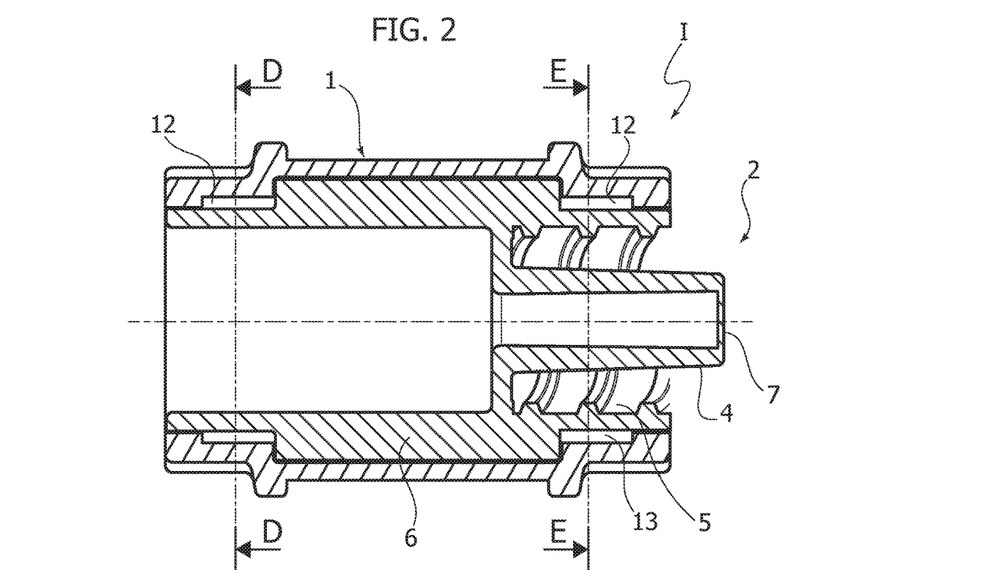
FIG. 2 is an axial section view according to the line C-C of FIG. 1.
Figure 3:
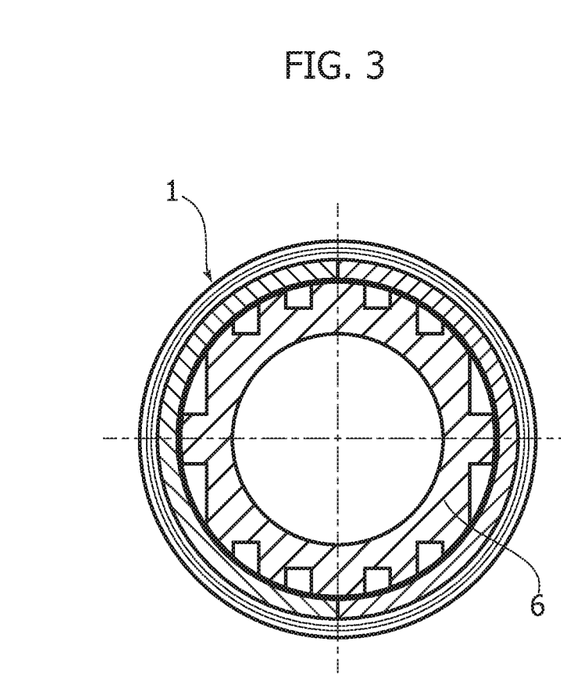
FIG. 3 is a cross sectional view according to the line B-B of FIG. 1.
Figure 4:
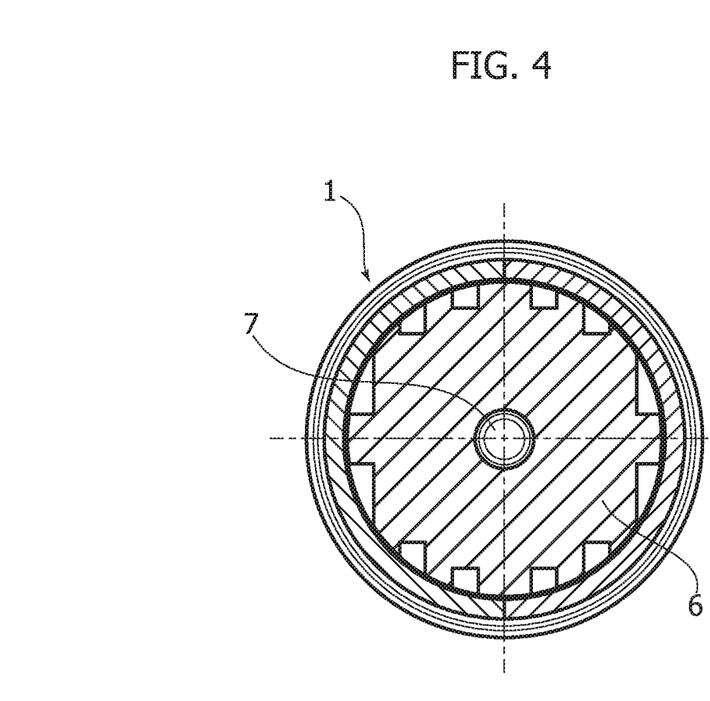
FIG. 4 is a cross sectional view according to the line A-A of FIG. 1.
Figure 5:
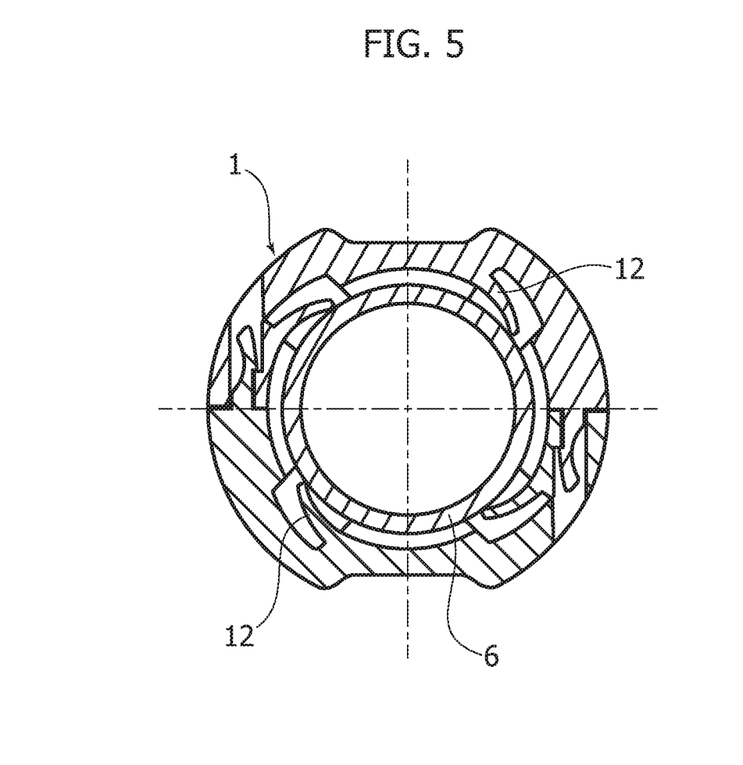
FIG. 5 is a cross sectional view according to the line D-D of FIG. 2.
Figure 6:
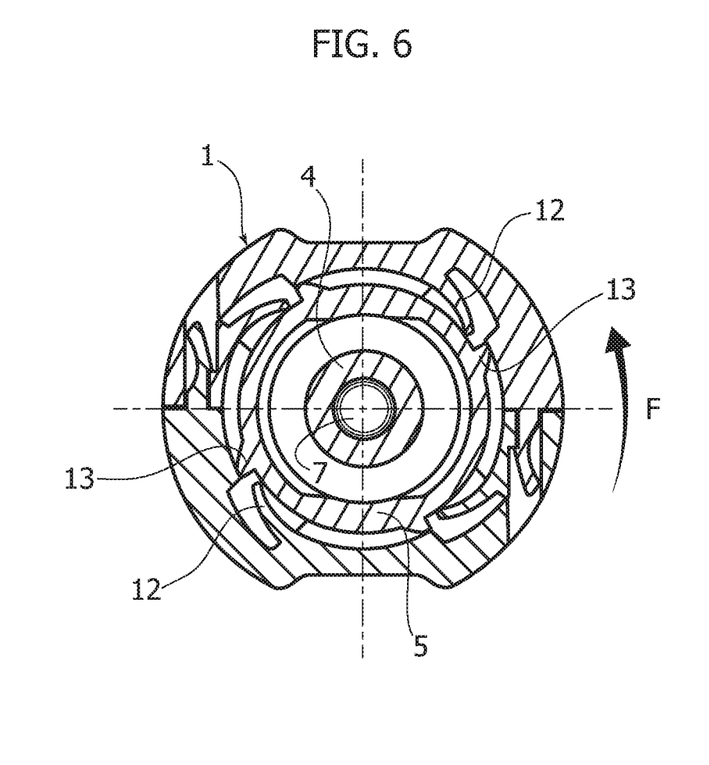
FIG. 6 is a cross sectional view according to the line E-E of FIG. 2.
Figure 7:
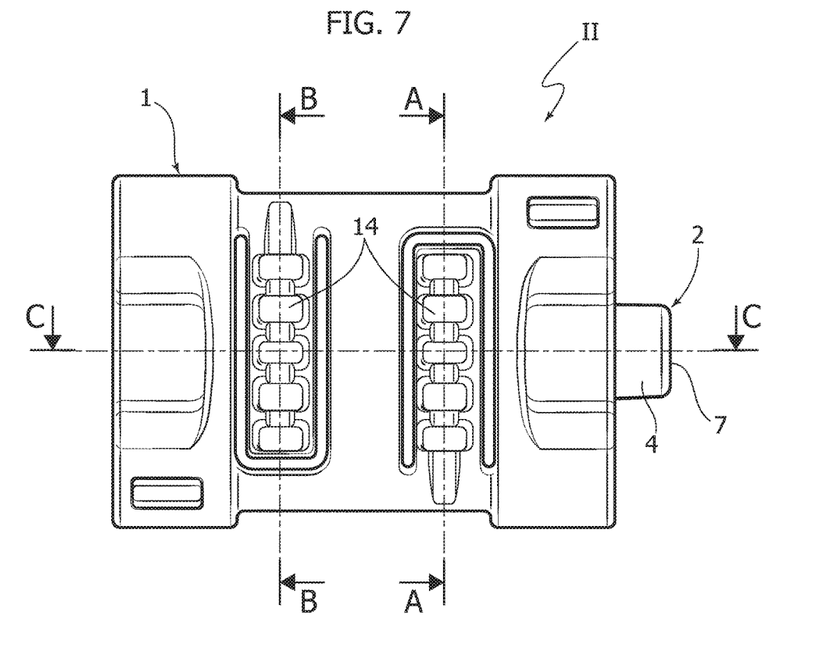
FIG. 7 is an elevational side view of a second embodiment of the cap according to the invention.
Figure 8:
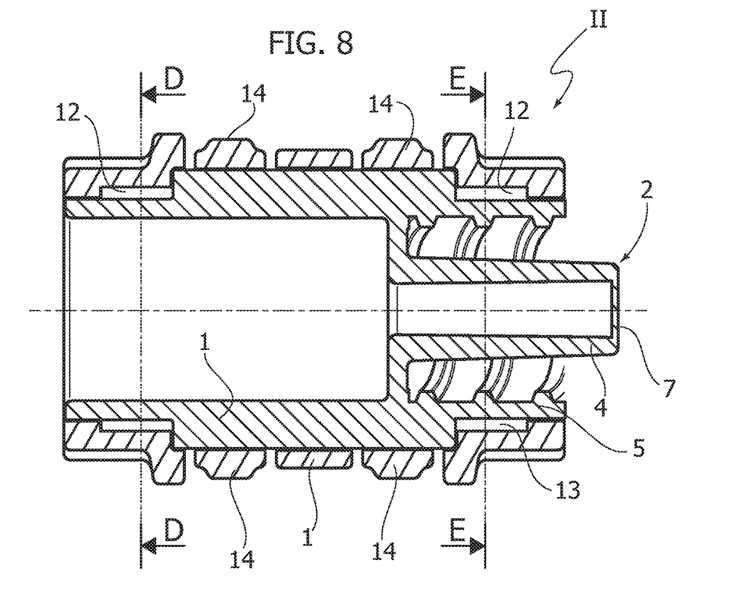
FIG. 8 is an axial section view according to the line C-C of FIG. 7.
Figure 9:
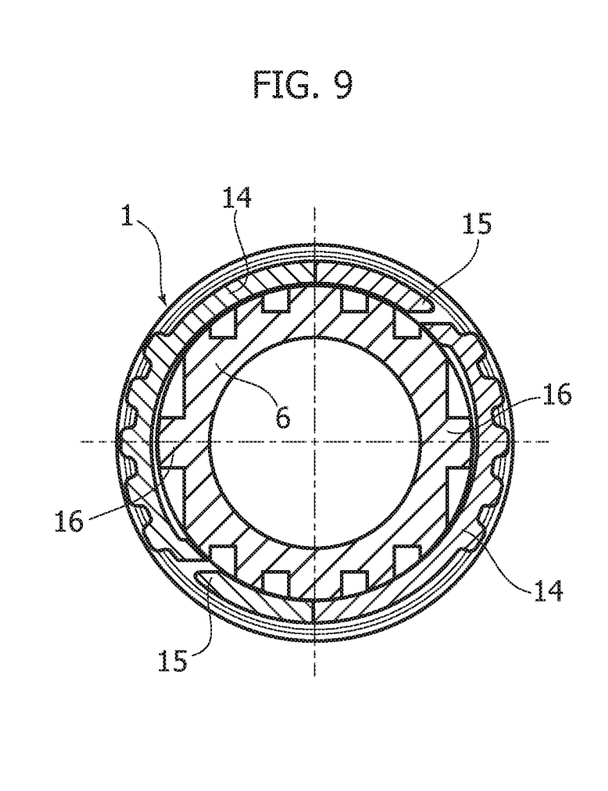
FIG. 9 is a cross sectional view along line B-B of FIG. 7.
Figure 10:
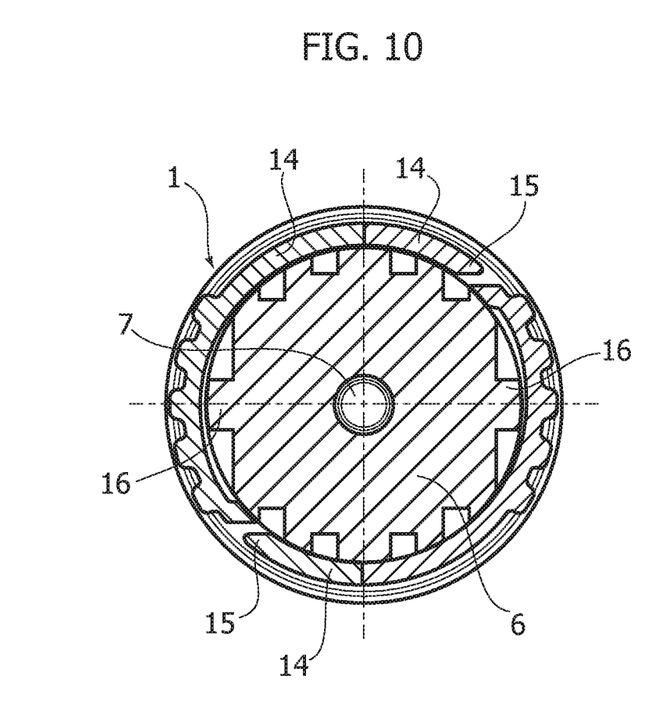
FIG. 10 is a cross sectional view along line A-A of FIG. 7.
Figure 11:
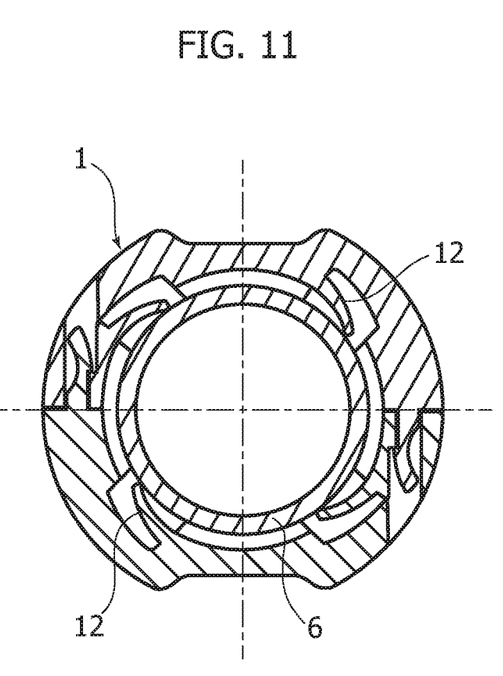
FIG. 11 is a cross sectional view along line D-D of FIG. 8.
Figure 12:
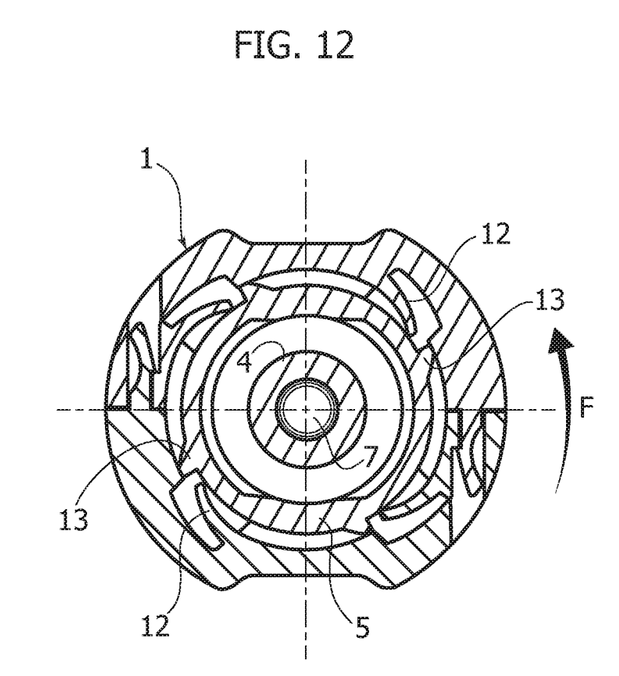
FIG. 12 is a cross sectional view along line E-E of FIG. 8.
Figure 13:
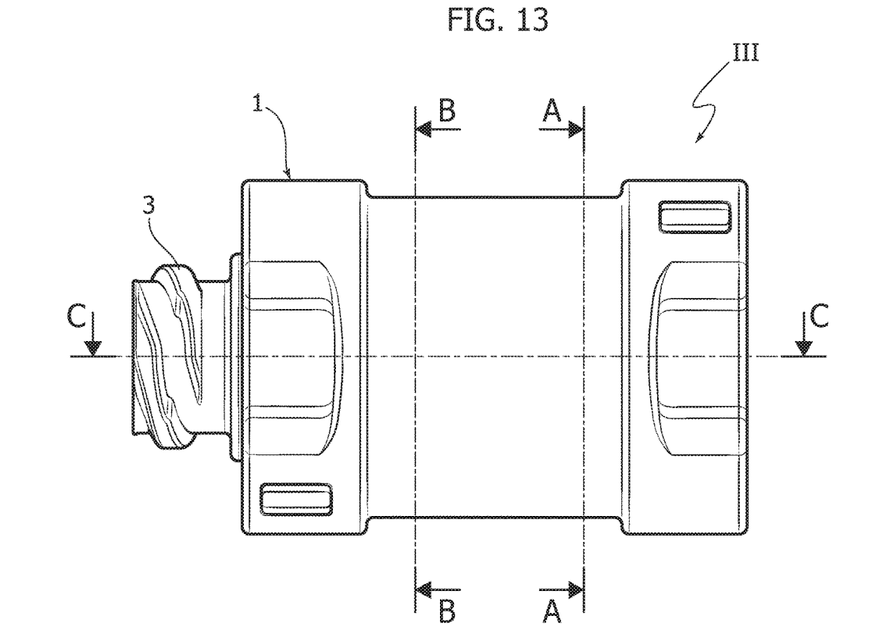
FIG. 13 is an elevational side view of a third embodiment of the cap according to the invention.
Figure 14:
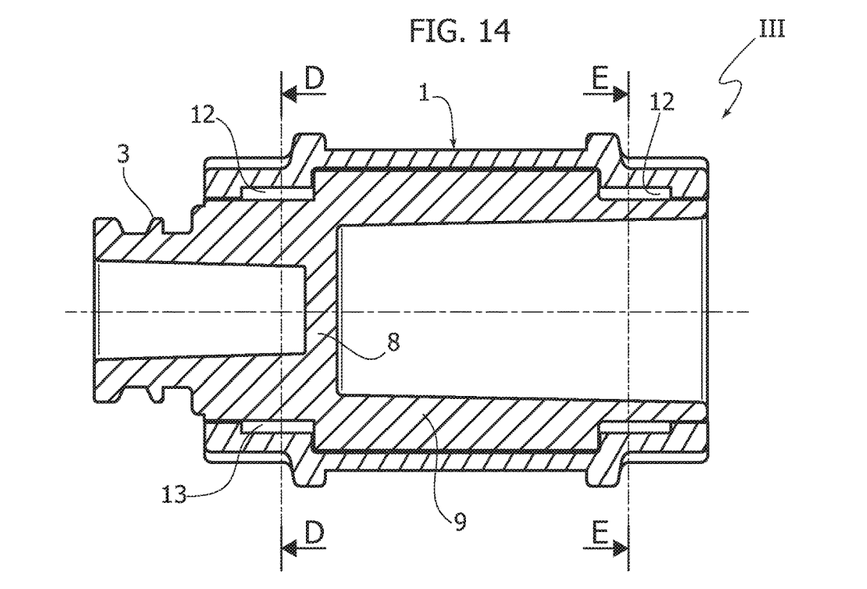
FIG. 14 is an axial section view according to the line C-C of FIG. 13.
Figure 15:
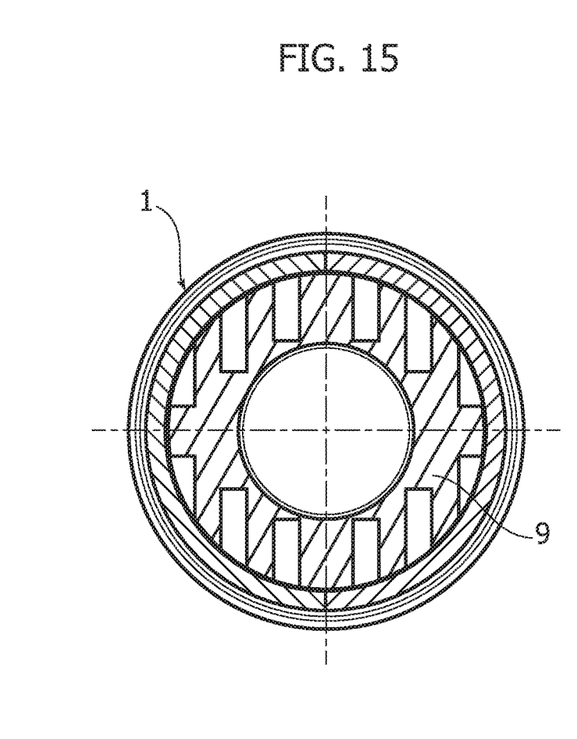
FIG. 15 is a cross sectional view along line B-B of FIG. 14.
Figure 16:
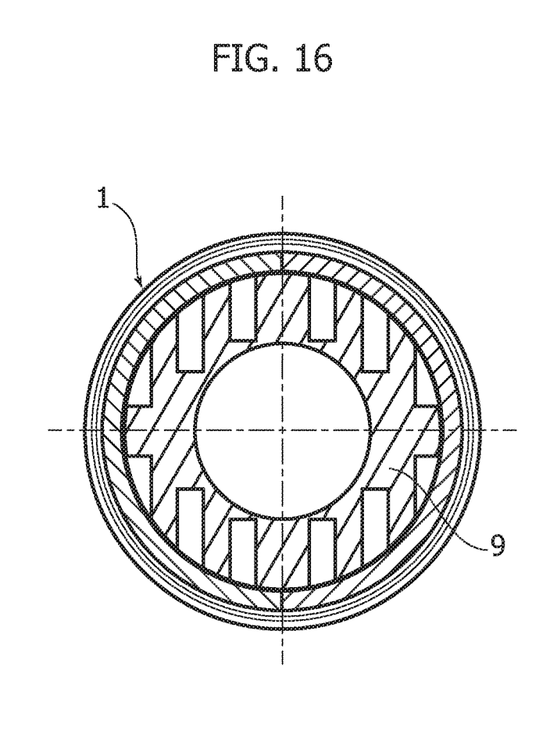
FIG. 16 is a cross sectional view along line A-A of FIG. 13.

In detail, and referring now to FIG. 6, the hollow body 1 is internally formed, on the side of the male connector 2, of a crown of elastically yielding ratchet teeth 12, cooperating by unidirectional coupling with corresponding projecting teeth 13 formed on the outside of the hollow element 5 of the male connector 2. The arrangement is such so that the hollow element 5, and therefore the entire male connector 2, is coupled in rotation with the hollow body 1 in the direction indicated by the arrow F in FIG. 6, due to the effect of the engagement between the teeth 12 and 13. The direction of rotation F corresponds to the screwing of the male connector 2 and a complementary female connector, assuming the hollow body 1 is kept stationary, and then the complementary female connector is rotated to screw it into the male connector 2. In the opposite direction of rotation, or rather, the unscrewing direction, the male connector 2 is freely rotatable with respect to the hollow body 1, due to the bounce of the yielding teeth 12 on the teeth 13, so that the complementary female connector cannot unscrew itself.

Obviously, in the case in which the hollow body 1 rotates and the complementary female connector is kept stationary, the situation is reversed, i.e. the direction of screwing is opposite to that of the arrow F, and the unscrewing direction is that of the arrow F.

In this way, during use, an accidental disengagement or due to incorrect operation, between the male connector 2 and the complementary female connector is prevented.

The variant of the safety cap represented in FIGS. 7 to 12, indicated by II, is analogous to the embodiment shown previously, and only the differences will now be described in detail, using the same numerical references for identical or similar parts.

This variant is configured to allow rotation of the male connector 2 corresponding to the unscrewing direction with respect to the complementary female connector but, as mentioned, only following a positive, or rather, voluntary operation. To this effect, the wall of the hollow body 1 is formed with a pair of elastically yielding locking segments 14, whose free ends 15 are suitable for engaging, as a result of a thrust applied to the segments 14, respective peripheral teeth formations 16 of the hollow appendage 6 (FIG. 10), so as to lock the rotation of the male connector 2 with respect to the body 1.

The variants of the cap according to the invention illustrated in FIGS. 13-18 and in FIGS. 19-24, and indicated with III and IV, respectively, correspond to the embodiments previously described with reference to FIGS. 1-6 and 7-12, respectively, with the only difference that the connector consists of a female connector 3, also of the luer-lock type and the like, instead of the male connector 2.

The female connector 3 is formed, in the usual manner, by an externally threaded tubular element with a conical inner surface, protruding from one end of the body 1 and, during use, is intended to be coupled to a complementary male connector of the luer-lock type or the like.

The female connector 3 is internally closed by a transverse wall 7, so that the flow passage through the cap III is, in this case as well, permanently obstructed in an inviolable manner. Moreover, the female connector 3 is integrally formed with a sleeve 9, analogous to the sleeve 6 of the preceding embodiments, locked axially in the body 1.

In a completely analogous manner to the embodiment already described, the composite formed by the female connector 2 and the sleeve 9 is coupled in rotation in one direction with the body 1 and is freely rotatable in the opposite direction. However, as will become evident, the rotation in the opposite direction may also possibly be locked, but only following a positive command imparted manually.

Figure 17:
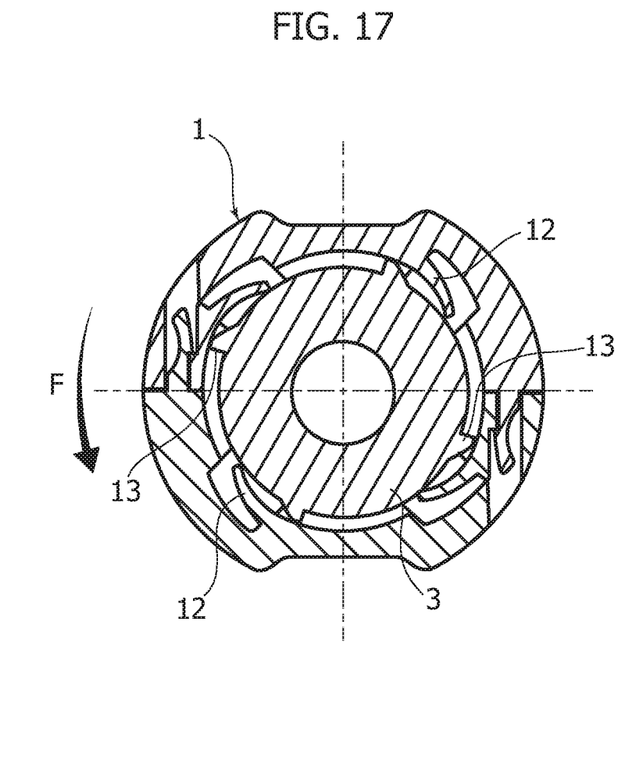
FIG. 17 is a cross sectional view along line D-D of FIG. 14.
Figure 18:
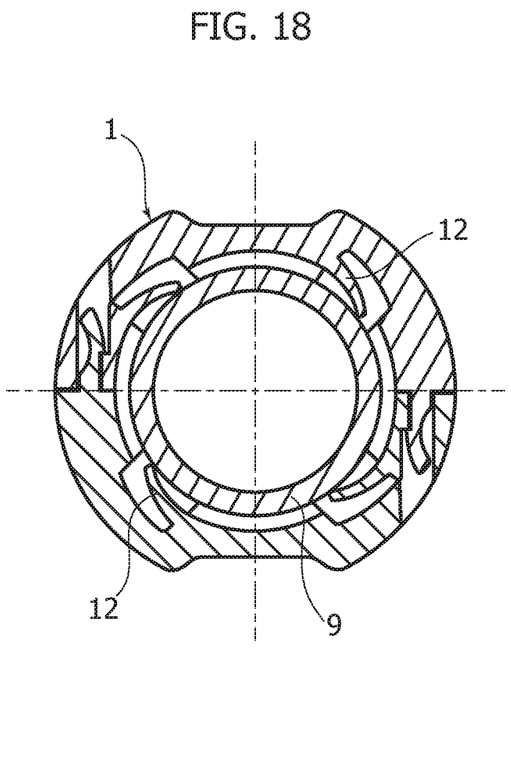
FIG. 18 is a cross sectional view along line E-E of FIG. 14.
Figure 19:
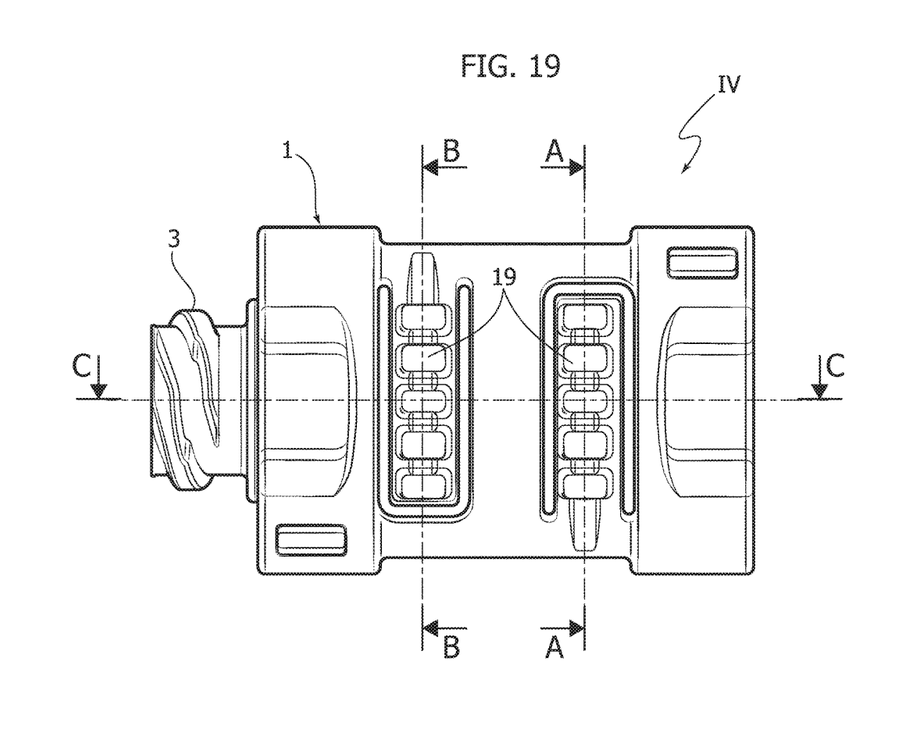
FIG. 19 is an elevational side view of a fourth embodiment of the cap according to the invention.
Figure 20:
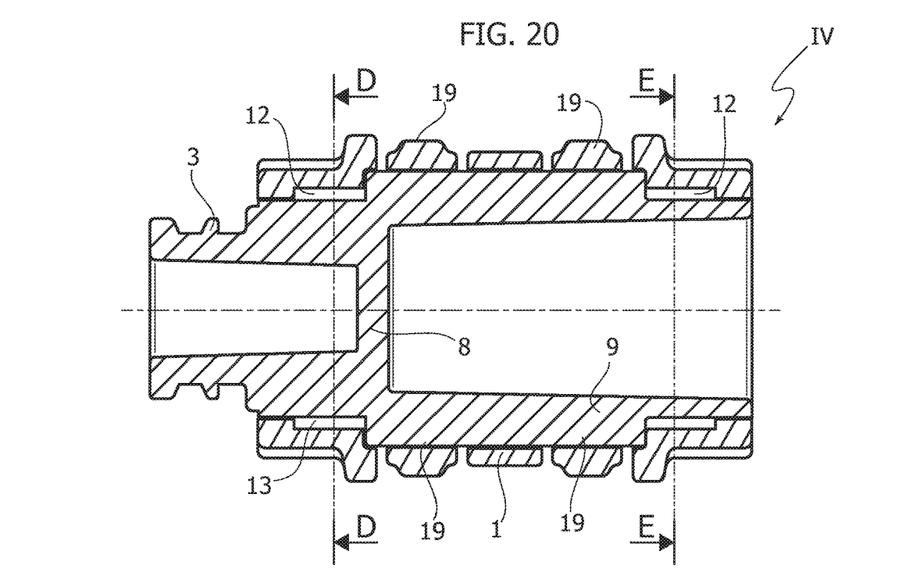
FIG. 20 is an axial section view according to the line C-C of FIG. 19.

In detail, and with reference to FIG. 17, the female connector 3 is coupled in rotation with the hollow body 1 in the direction indicated by the arrow F, corresponding to the screwing of this female connector 3 with a complementary male connector, rotating the hollow body 1, while it is normally freely rotatable in the opposite direction, or rather, in the unscrewing direction. To this effect, the hollow body 1, as for the embodiments previously described, is formed with a series of elastically yielding ratchet teeth 12, cooperating by unidirectional coupling with corresponding projecting teeth 13 formed outside the female connector 3.

Figure 21:
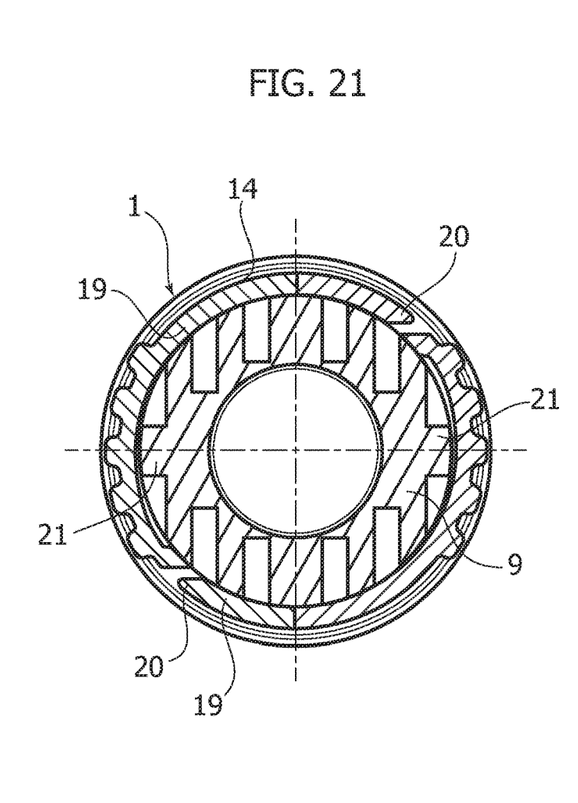
FIG. 21 is a cross sectional view along line B-B of FIG. 19.
Figure 22:
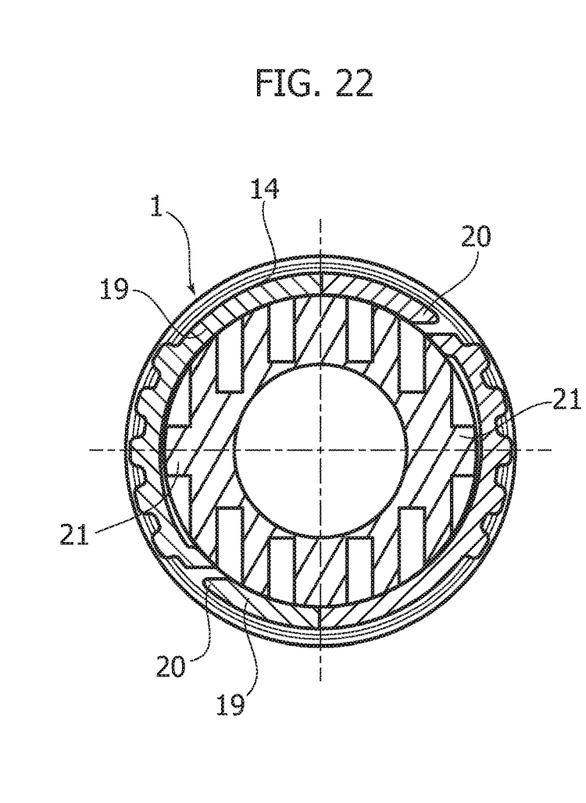
FIG. 22 is a cross sectional view along line A-A of FIG. 19.
Figure 23:
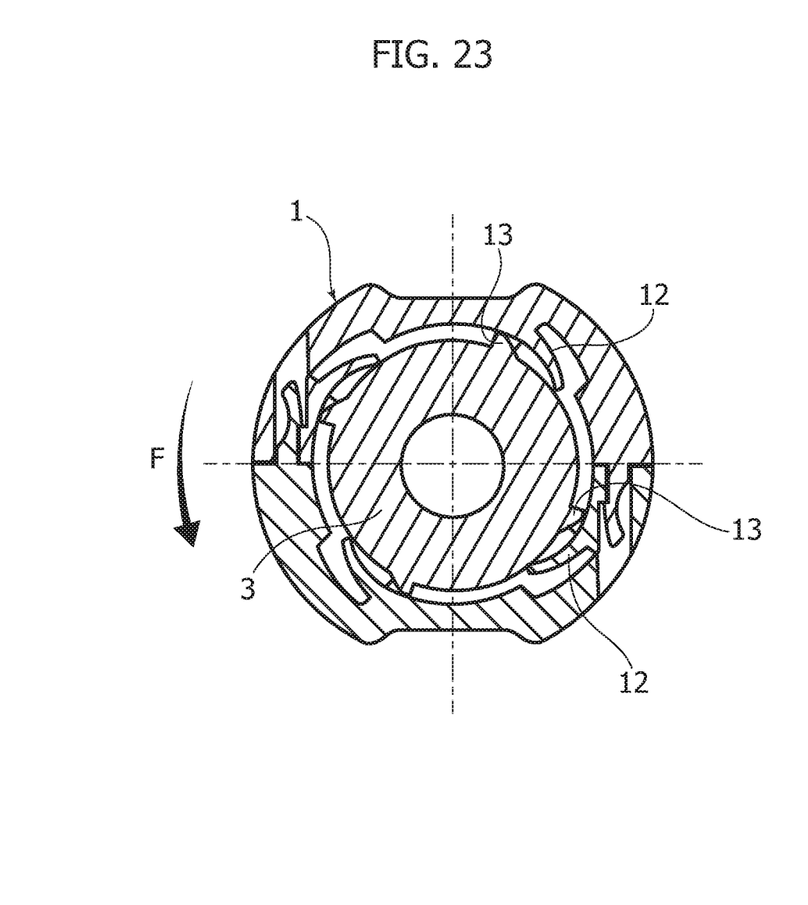
FIG. 23 is a cross sectional view along line D-D of FIG. 20.
Figure 24:
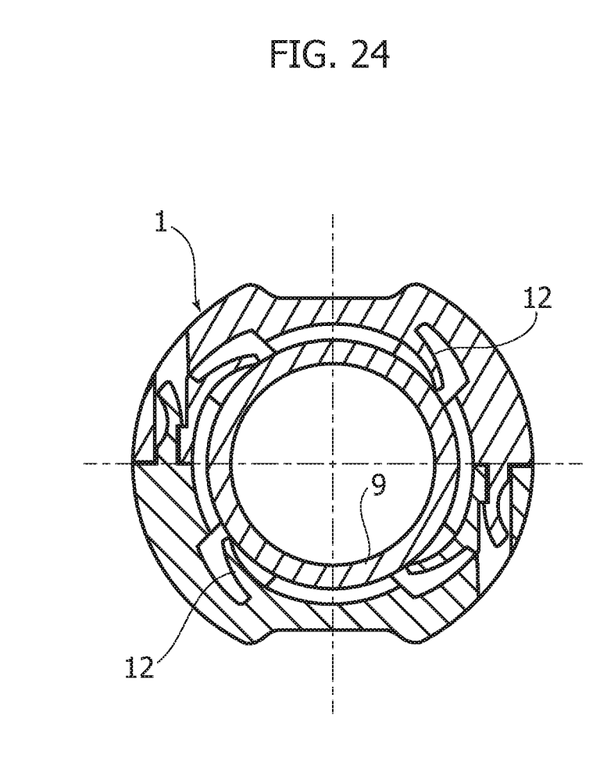
FIG. 24 is a cross sectional view along line E-E of FIG. 20.

The variant illustrated in FIGS. 19 to 24 is configured, in a manner corresponding to the embodiment of FIGS. 7 to 12, for possibly locking in rotation the female connector 3, with respect to the hollow body 1, in the direction opposite to that indicated by the arrow F, in this case as well, by a positive command imparted manually. To this effect, the hollow body 1 of the cap IV is therefore formed with one or two pairs of elastically yielding locking segments 19, analogous to the yielding locking sectors 14, the free ends 20 of which are suitable for engaging respective peripheral teeth formations 21 of the sleeve 9 (FIGS. 21 and 22).

Of course, the details of construction and the embodiments may be widely varied with respect to those described and illustrated, without departing from the scope of the present invention as defined in the following claims.

The invention claimed is:

1. A cap for medical fluid lines, comprising:
   a hollow body within which a connector accessible at one end of the body is coaxially housed;
   unidirectional coupling means to lock the connector in rotation with respect to the body in a direction corresponding to a screwing of said connector and a complementary connector to be coupled therewith, and to enable free rotation of said connector in the opposite direction; and
   said connector having a wall closing a free end thereof to inviolably obstruct a passage through said body permanently to avoid fluid communication with an interior of said hollow body when said connector is coupled to said complementary connector.

2. A cap according to claim 1, further comprising locking means designed to be positively operated to lock said connector in rotation with respect to the body in said opposite direction.

3. A cap according to claim 1, wherein said unidirectional coupling means comprise ratchet teeth.

4. A cap according to claim 2, wherein said locking means comprise elastically yielding segments of the body, suitable for engaging corresponding peripheral teeth of said connector.

5. A cap according to claim 1, wherein the connector is a male luer lock connector, having an internally threaded outer hollow element and an inner hollow element having a transverse partition for closing the flow through the cap.

6. A cap according to claim 1, wherein the connector is a female luer lock connector having an externally threaded hollow element and a transverse partition for closing the flow through the cap.

7. A cap according to claim 1, wherein the connector is integrally formed with a sleeve, axially locked within said body.

* * * * *